(12) United States Patent
Tozeski

(10) Patent No.: US 11,259,640 B2
(45) Date of Patent: Mar. 1, 2022

(54) ARM SUPPORT FOR BLOOD PRESSURE MONITORING

(71) Applicant: Chester Tozeski, Shrewsbury, MA (US)

(72) Inventor: Chester Tozeski, Shrewsbury, MA (US)

( * ) Notice: Subject to any disclaimer, the term of this patent is extended or adjusted under 35 U.S.C. 154(b) by 0 days.

(21) Appl. No.: 16/524,126

(22) Filed: Jul. 28, 2019

(65) Prior Publication Data

US 2020/0054286 A1 Feb. 20, 2020

Related U.S. Application Data

(60) Provisional application No. 62/711,881, filed on Jul. 30, 2018.

(51) Int. Cl.
| | |
|---|---|
| *A47C 16/00* | (2006.01) |
| *F16M 11/24* | (2006.01) |
| *F16M 11/28* | (2006.01) |
| *A61B 5/00* | (2006.01) |

(52) U.S. Cl.
CPC .............. *A47C 16/00* (2013.01); *A61B 5/702* (2013.01); *F16M 11/245* (2013.01); *F16M 11/28* (2013.01)

(58) Field of Classification Search
CPC ..... A61B 5/021; A61B 5/02141; A61B 5/702; A61B 2560/0431; A61G 13/1235; A61G 13/124; A61G 13/1245; A47C 16/00; A47C 16/02; A47C 16/025; F16M 11/24; F16M 11/242; F16M 11/245; F16M 11/247; F16M 11/26; F16M 11/28; F16M 11/30; F16M 11/32; F16M 11/34; F16M 11/36

See application file for complete search history.

(56) References Cited

U.S. PATENT DOCUMENTS

| | | | | |
|---|---|---|---|---|
| 711,550 A | * | 10/1902 | Zibulski ............. | A61G 13/1235 5/646 |
| 1,260,929 A | * | 3/1918 | Maxey ................... | A47C 16/00 297/394 |
| 1,891,755 A | * | 12/1932 | Davis ..................... | A61G 13/12 602/39 |
| 2,552,370 A | * | 5/1951 | Curtis ................ | A61G 13/1245 5/648 |
| 2,732,269 A | * | 1/1956 | Astroff .................... | A61G 13/12 5/646 |
| 3,225,656 A | * | 12/1965 | Flaherty ................. | F41A 23/16 89/37.04 |

(Continued)

FOREIGN PATENT DOCUMENTS

CN 106388382 A * 2/2017

*Primary Examiner* — Jonathan Liu
*Assistant Examiner* — Guang H Guan
(74) *Attorney, Agent, or Firm* — Brian M. Dingman; Dingman IP Law, PC

(57) ABSTRACT

An arm support for blood pressure monitoring, including an adjustable-height stand with a number of legs that support an upwardly-extending post. An arm-supporting saddle is fixed in position at the top of the post. The saddle has an upper arm-support surface that is configured to support an arm of a user. The top of the post is adjustable in height relative to the legs, to allow the saddle to be positioned at an appropriate height such that the user's arm when supported by the saddle is in a horizontal position.

20 Claims, 8 Drawing Sheets

(56) References Cited

U.S. PATENT DOCUMENTS

| | | | | |
|---|---|---|---|---|
| 3,313,505 A * | 4/1967 | Petrie | B25H 1/00 | 248/165 |
| 4,565,409 A * | 1/1986 | Hollonbeck | A47C 16/00 | 297/411.1 |
| 4,909,264 A * | 3/1990 | Wadsworth, III | A61G 13/12 | 128/845 |
| 4,988,064 A * | 1/1991 | Hoshino | F16M 11/2057 | 248/170 |
| 5,201,319 A * | 4/1993 | Negishi | A61B 5/022 | 600/485 |
| 5,403,269 A * | 4/1995 | Kennedy | A61H 1/006 | 482/122 |
| 5,884,974 A * | 3/1999 | Bergsten | A47C 1/0308 | 297/411.35 |
| 6,102,344 A * | 8/2000 | Kasvin | A61B 90/60 | 248/118 |
| 6,142,460 A * | 11/2000 | Irwin | B25B 5/10 | 269/37 |
| 6,305,117 B1 * | 10/2001 | Hales, Sr. | F41A 23/02 | 42/94 |
| 6,626,408 B1 * | 9/2003 | Lorbiecki | A61B 6/0421 | 248/279.1 |
| RE38,369 E * | 12/2003 | Ruckstadter | A47B 21/0371 | 248/118.3 |
| 6,920,713 B1 * | 7/2005 | Love | F41A 23/04 | 42/90 |
| D518,894 S * | 4/2006 | Kim | A61B 5/022 | D24/184 |
| 7,673,836 B2 * | 3/2010 | Wallock | A47C 16/00 | 248/118 |
| D627,033 S * | 11/2010 | Hicks | A61G 13/101 | D22/199 |
| 7,934,687 B2 * | 5/2011 | Crook | A61F 5/3761 | 248/168 |
| D655,418 S * | 3/2012 | Hancock | A47C 16/00 | D24/183 |
| 8,269,090 B2 * | 9/2012 | Russell | G09B 15/06 | 84/469 |
| D698,888 S * | 2/2014 | Hicks | F41A 23/02 | D22/199 |
| 8,656,917 B2 * | 2/2014 | Gamber | A61F 5/3761 | 128/845 |
| D728,798 S * | 5/2015 | Moon | F16M 11/2057 | D24/184 |
| 9,314,390 B2 * | 4/2016 | Hernandez | B67B 7/16 | |
| 10,172,468 B2 * | 1/2019 | Houghson | A47C 16/00 | |
| 10,555,613 B1 * | 2/2020 | Harris | A47C 16/025 | |
| 10,774,951 B2 * | 9/2020 | Ball | F16B 7/185 | |
| 10,806,650 B2 * | 10/2020 | Di Lauro | A61G 13/101 | |
| 2020/0054286 A1 * | 2/2020 | Tozeski | A61B 5/702 | |

\* cited by examiner

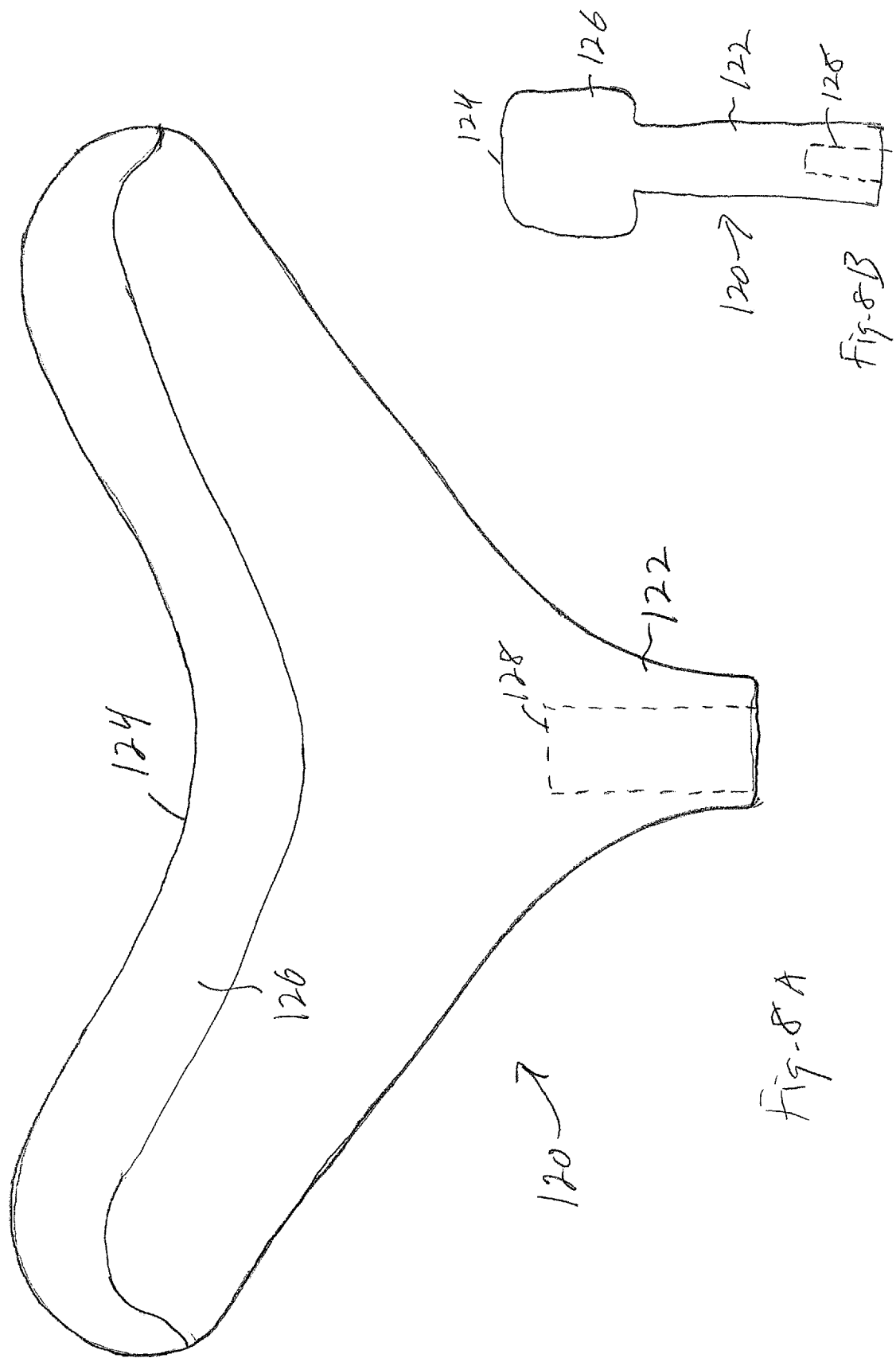

ARM SUPPORT FOR BLOOD PRESSURE MONITORING

CROSS-REFERENCE TO RELATED APPLICATION

This application claims priority to Provisional Patent Application 62/711,881, filed on Jul. 30, 2018.

BACKGROUND

This disclosure relates to an adjustable-height stand that supports an arm around the elbow region while the person's blood pressure is being taken using a cuff that is engaged with the upper arm.

When blood pressure is being taken using a sphygmomanometer, with the cuff placed over the upper arm, the arm should be supported in a horizontal position, with the upper arm free for use by a medical professional to take the blood pressure. It is known that if the arm is not horizontal the blood pressure reading will be incorrect. Accuracy can be critical when it comes to diagnosing and treating medical conditions (such as high blood pressure) that are related to or associated with a measured blood pressure.

SUMMARY

Featured in this disclosure is an arm support for blood pressure monitoring. The stand can accommodate a sitting or standing user, and comfortably support the arm at about shoulder height. The stand is thus very helpful to taking an accurate blood pressure reading. Also, the stand allows the user to be in the same position each time a blood pressure reading is taken, and thus helps to ensure repeatable readings.

The arm support has an adjustable-height stand comprising a plurality of legs that support an upwardly-extending post that lies along a longitudinal post axis, wherein the legs are configured to be collapsed and deployed relative to the post, wherein when the legs are deployed they are spaced radially from the bottom end of the post and their ends are spaced from the post axis, and when the legs are collapsed their ends move closer to the post axis. There is an arm-supporting saddle at the top of the post, wherein the saddle is configured to support an arm of a user at or just above or below the elbow region. The top of the post is adjustable in height relative to the legs, to allow the saddle to be positioned at an appropriate height such that the user's arm when supported by the saddle is in a horizontal position.

The saddle may be approximately 4 inches high, 1.5 inches thick and 7.5 inches wide. The saddle may be generally "U"-shaped along its width, to define a low point in the middle of the width that is configured to support the user's arm. The saddle may be generally "V"-shaped from a side view. The saddle may comprise a padded region that supports the arm. The saddle padded region may comprise a textured upper surface, to provide some grip of the arm.

The post may comprise a plurality of interconnected post sections that fit together telescopically, to accomplish the adjustable height. The post longitudinal axis may be vertical. The post longitudinal axis may be angled from the vertical. The post longitudinal axis may be angled toward the user, so that the legs are farther from the user than is the saddle.

In one aspect, an arm support for blood pressure monitoring includes an adjustable-height stand comprising a plurality of legs that support an upwardly-extending post that lies along a longitudinal post axis, wherein the legs are configured to be collapsed and deployed relative to the post, wherein when the legs are deployed they are spaced radially from the bottom end of the post and their ends are spaced from the post axis, and when the legs are collapsed their ends move closer to the post axis, an arm-supporting saddle that is carried at the top of the post, wherein the saddle has an upper arm-support surface that is configured to support an arm of a user at around the elbow region, and wherein the top of the post is adjustable in height relative to the legs, to allow the saddle to be positioned at an appropriate height such that the user's arm when supported by the saddle is in a horizontal position.

Examples may include one of the above and/or below features, or any combination thereof. The saddle may be generally "U"-shaped along its width, to define a low point in the middle of the width that is configured to support the user's arm. The saddle may be thicker at a top portion that defines the arm support surface than it is at a lower portion that is coupled to the post, to define a wide arm-support surface. The saddle may be generally "V"-shaped from a side view. The saddle may comprise a region that supports the arm. The arm-support surface of the saddle may be textured, to provide some grip of the arm. The saddle may be approximately 4 inches high, 1.5 inches thick and 7.5 inches wide.

Examples may include one of the above and/or below features, or any combination thereof. The post may comprise a plurality of interconnected post sections that fit together telescopically, to accomplish the adjustable height. The post longitudinal axis may be vertical. The post longitudinal axis may be angled from the vertical. The post longitudinal axis may be angled toward the user, so that the legs are farther from the user than is the saddle.

In another aspect, an arm support for blood pressure monitoring includes an adjustable-height stand comprising a plurality of legs that support an upwardly-extending post that lies along a longitudinal post axis, wherein the legs are configured to be collapsed and deployed relative to the post, wherein when the legs are deployed they are spaced radially from the bottom end of the post and their ends are spaced from the post axis, and when the legs are collapsed their ends move closer to the post axis, an arm-supporting saddle that is carried at the top of the post, wherein the saddle has an upper arm-support surface that is configured to support an arm of a user at around the elbow region, wherein the saddle is generally "U"-shaped along its width, to define a low point in the middle of the width that is configured to support the user's arm, wherein the saddle is thicker at a top portion that defines the arm support surface than it is at a lower portion that is coupled to the post, to define a wide arm-support surface, wherein the saddle is generally "V"-shaped from a side, and wherein the arm-support surface of the saddle is textured, to provide some grip of the arm, and wherein the top of the post is adjustable in height relative to the legs, to allow the saddle to be positioned at an appropriate height such that the user's arm when supported by the saddle is in a generally horizontal position, wherein the post comprises a plurality of interconnected post sections that fit together telescopically, to accomplish the adjustable height, and wherein the post longitudinal axis is configured to be generally vertical.

BRIEF DESCRIPTION OF THE DRAWINGS

FIG. 8A is a front view and FIG. 8B a side view of another saddle for an arm support for blood pressure monitoring.

DETAILED DESCRIPTION

Figure 1:
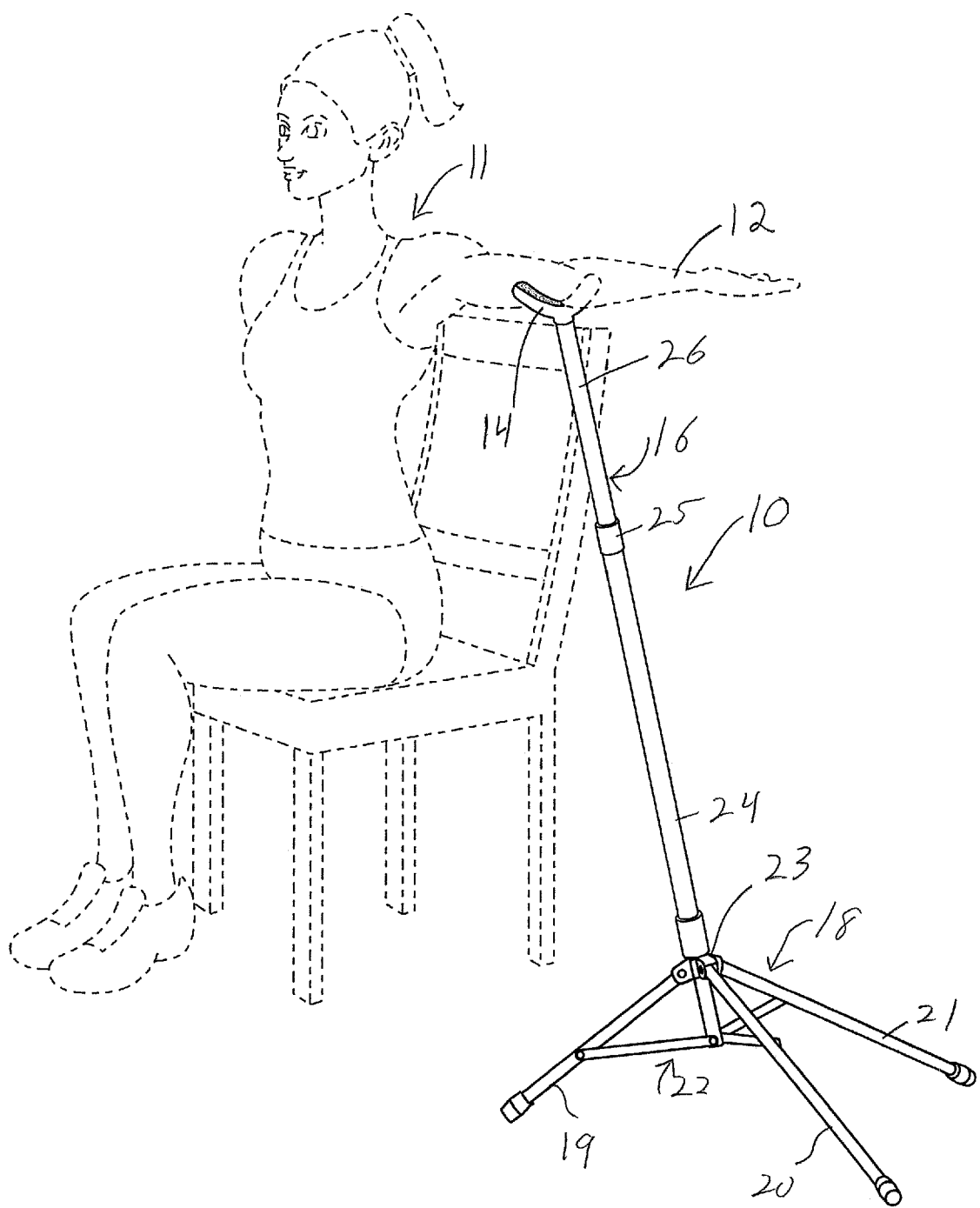
FIG. 1 is an illustration of an arm support for blood pressure monitoring.

Arm support for blood pressure monitoring 10 is shown in FIG. 1. Arm support 10 includes collapsible stand 18 that supports adjustable-height post 16. Arm-supporting saddle 14 is carried at the top of post 16. Saddle 14 is generally "U"-shaped so as to accommodate and support arm 12 of user 11. Generally the arm should be supported in the elbow region as shown. This leaves the upper arm free for use by a medical professional to take the blood pressure. Generally, a sphygmomanometer is used, and the cuff can be placed over the free upper arm. Since the height of saddle 14 is adjustable, arm support 10 is able to be adjusted such that the arm is horizontal, as shown in the drawing. It is known that if the arm is not horizontal the blood pressure reading will be incorrect. Accordingly, a stand that can accommodate a sitting or standing user, and comfortably support the arm at about shoulder height, is very helpful to taking an accurate blood pressure reading. Accuracy can be critical when it comes to diagnosing and treating medical conditions (such as high blood pressure) that are related to or associated with a measured blood pressure. Also, the stand allows the user to be in the same position each time a blood pressure reading is taken, and thus helps to ensure repeatable readings.

Figure 5A:
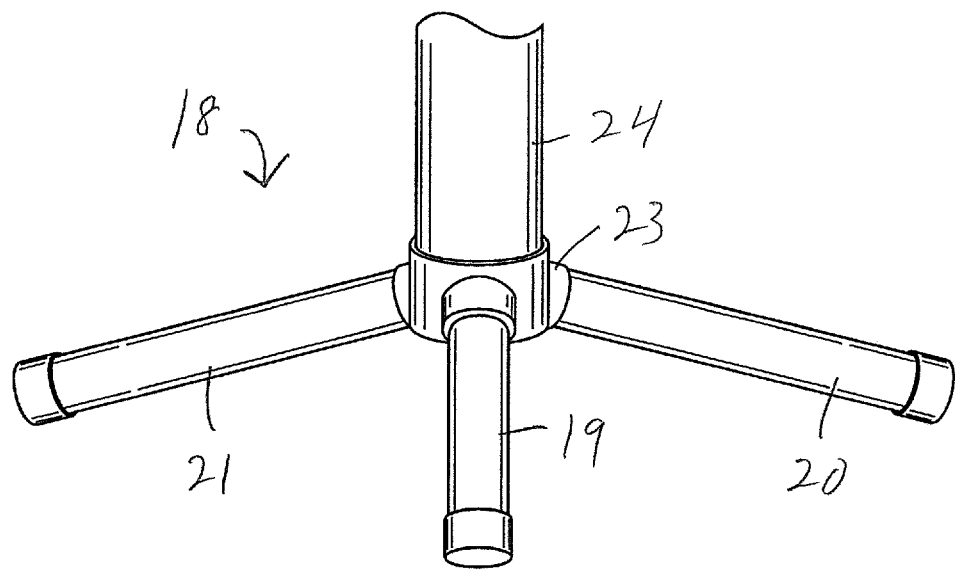
FIG. 5A is a partial front view and FIG. 5B is a bottom view of a stand for the pole of the arm support for blood pressure monitoring.
Figure 5B:
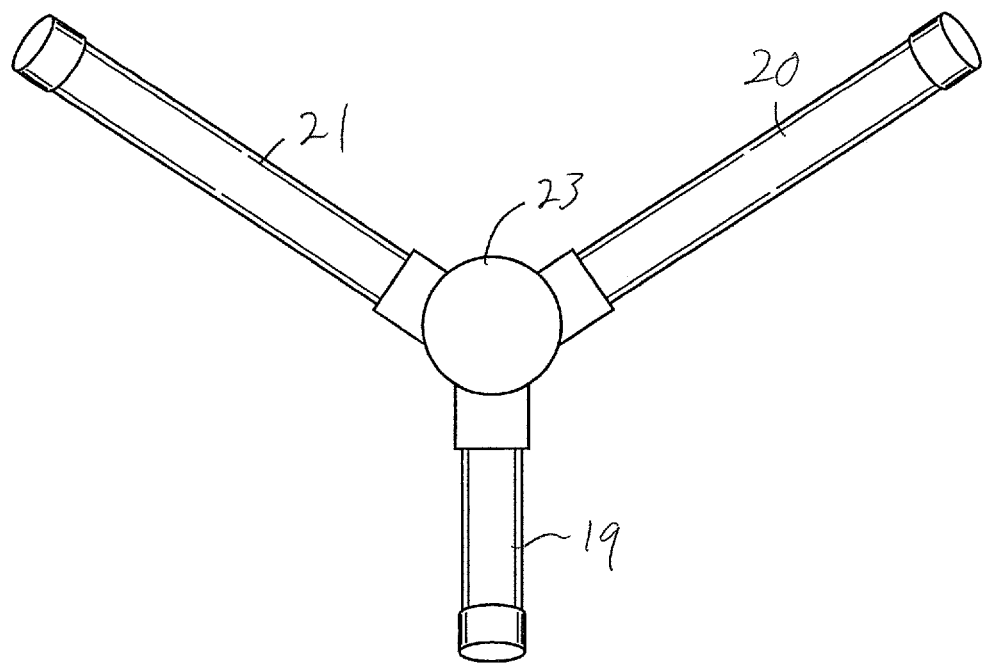

Stand 18 in this non-limiting example includes legs 19-21 that are supported from central knuckle 23 by pivoting arms set 22. This arrangement allows the legs to be folded up so that their ends (which normally sit on the floor) are closer to the longitudinal axis of the post 16, to present a more narrow form factor, for storing the collapsed arm support stand. See also FIGS. 5A and 5B.

Figure 2A:
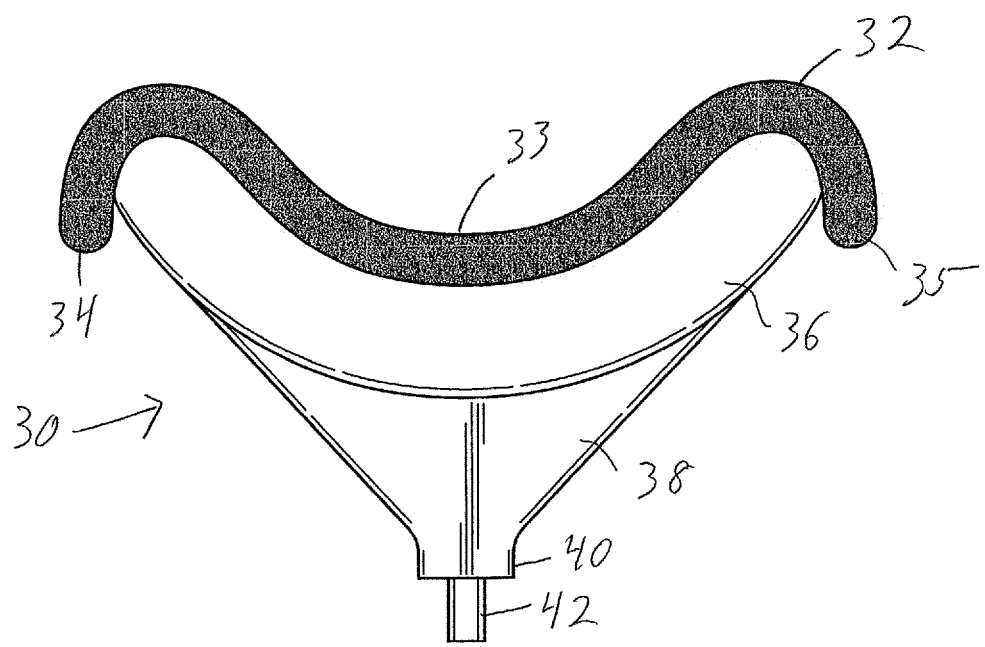
FIG. 2A is a front view and FIG. 2B is a side view of a saddle for the arm support for blood pressure monitoring.
Figure 2B:
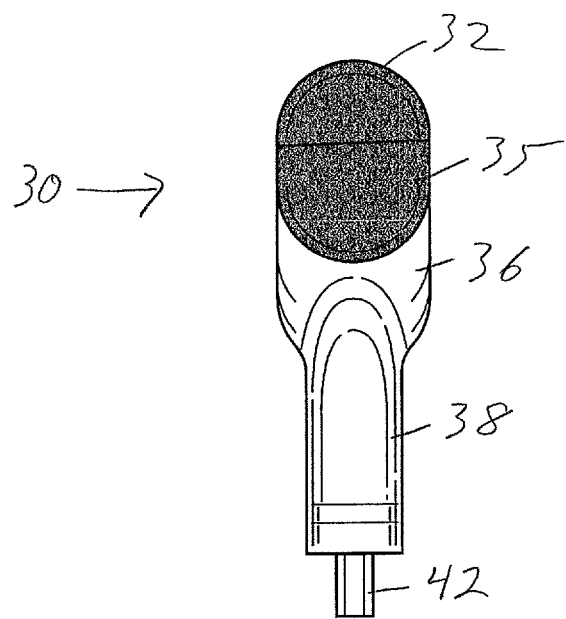
Figure 3:
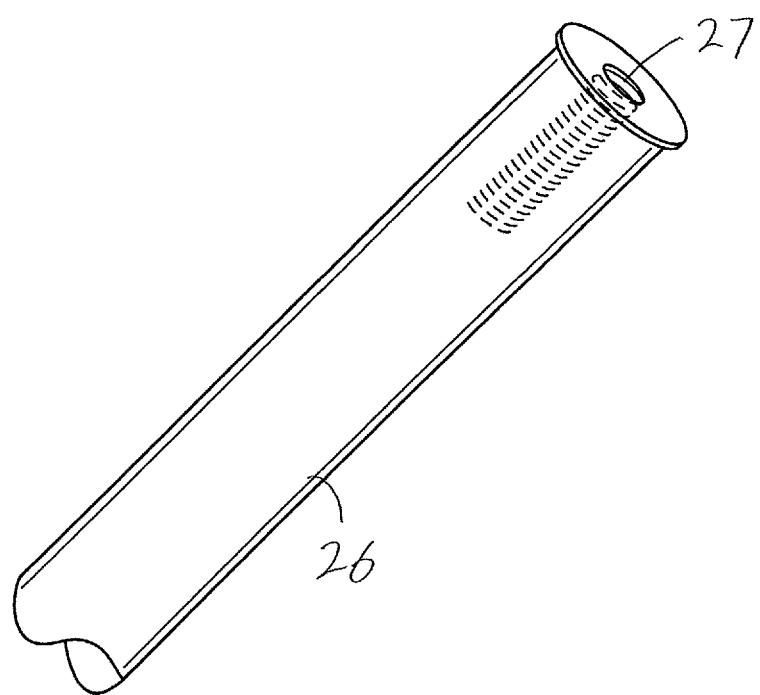
FIG. 3 is a partial view of the top of a pole of the arm support for blood pressure monitoring.
Figure 4:
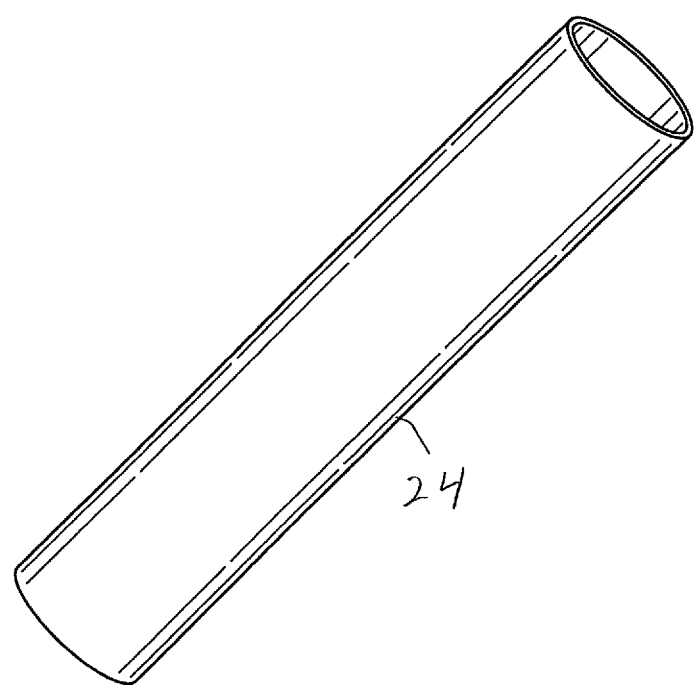
FIG. 4 is a partial view of a pole of the arm support for blood pressure monitoring.

Height adjustment is accomplished by pole 16 being adjustable in length. Length adjustability can be accomplished in a desired fashion. In this non-limiting example pole 26 is telescopically received in pole 24. Twist lock 25 locks and releases pole 26 to allow it to be moved up and down as necessary to place saddle 14 at the correct height. Saddle 14 is carried at the end of pole 26. The interconnection of the saddle and the support pole can be accomplished in a desired manner, for example as is depicted in FIGS. 2 and 3. Saddle 30 has lower stub or pin 42 (FIG. 2) that fits into cavity 27 at the top end of pole 26 (FIG. 3). Alternatively, the saddle can have a cavity into which the top of the pole fits. Cavity 27 can be threaded and stub 42 can be threaded, or not. It is preferable to make saddle 30 removable from the pole, in part so that the saddle can be replaced if necessary. Or, the saddle can be permanently mounted to the pole by any mechanical means.

Saddle 30 comprises support cushion 36 that is topped by textured surface 32 with ends 34 and 35 that roll over the ends of the cushion, as shown, which can improve the appearance. Low point 33 is typically where the user's elbow would rest. Support structure 38 tapers evenly to lower area 40 from which stub 42 projects. The wide, tapered support structure lends more stability to the arm support.

Figure 6:
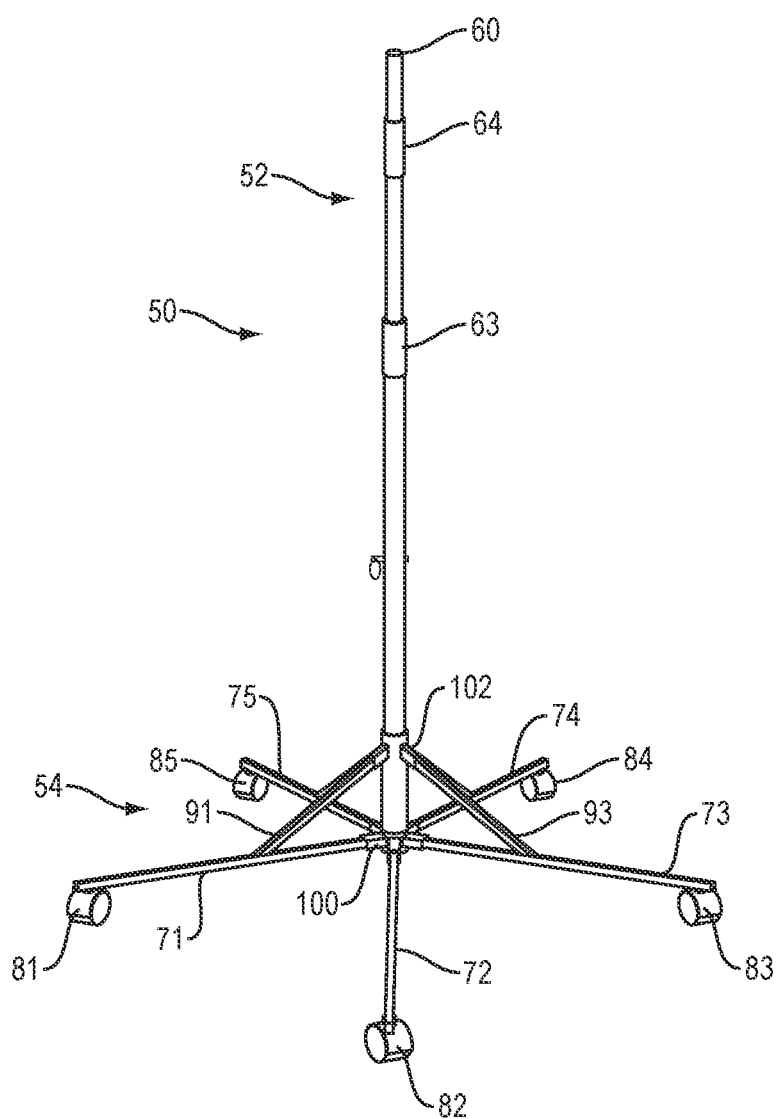
FIG. 6 shows a different stand, without the arm support
Figure 7:
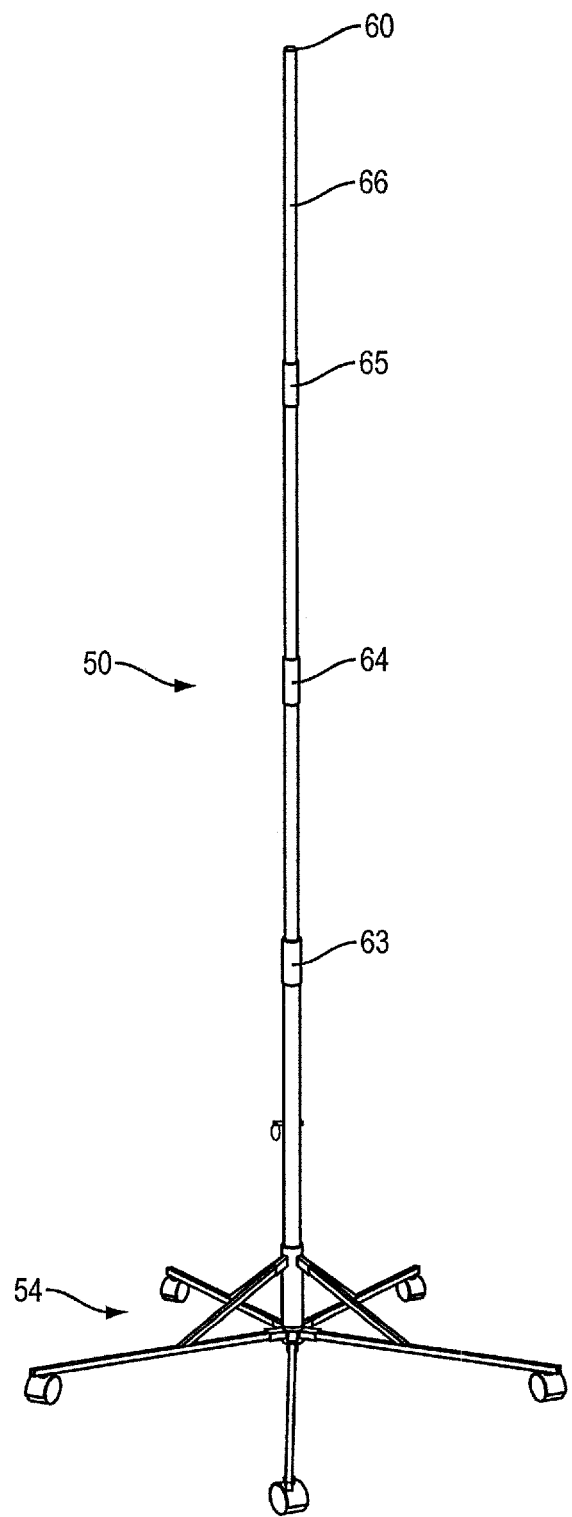
FIG. 7 shows the stand of FIG. 6 extended higher.

The arm support 50 can alternatively have a pole 52 that is vertical, as shown in FIGS. 6 and 7. Pole 52 is collapsed in FIG. 6 and extended in FIG. 7. Pole 52 is vertical rather than tipped. A vertical pole can allow the stand to be located closer to the user's chair. Also, it takes less floor space that an arm support with a tilted pole. Arm support 50 includes stand 54 with legs 71-75 that have casters 81-85, to allow the arm support to be rolled/moved around. Knuckles 100 and 102 support the legs and the intermediate supports 91 and 93, to allow the legs to be collapsed and deployed. Pole 52 is telescopic and includes interfitted poles with releasable locks 63, 64 and 65 between them. Upper pole 66 is configured to interface to and support a saddle, not shown in FIGS. 6 and 7, at the top 60 thereof.

FIGS. 8A and 8B illustrate another saddle 120 with lower portion 122 that defines cavity 128 that receives the top of the post (not shown). Upper surface 124 is configured to support the arm; it can be textured to better grip the arm. Upper lip 126 can define a wider section that offers more support for the arm but maintains a lower thickness (profile) of lower portion 122. Saddle 120 can be molded from plastic and it can be permanently or removably attached to the top of the post.

A number of implementations have been described. Nevertheless, it will be understood that additional modifications may be made without departing from the scope of the inventive concepts described herein, and, accordingly, other embodiments are within the scope of the following claims.

What is claimed is:

1. An arm support adapted to be used for blood pressure monitoring, the arm support comprising:
   an adjustable stand comprising:
      a plurality of legs; and
      an upwardly extending post that is supported by the plurality of legs and lies along a longitudinal post axis;
      wherein the adjustable stand has an adjustable height;
      wherein the upwardly extending post defines an attachment portion at a top end of the upwardly extending post;
      wherein the attachment portion defined by the upwardly extending post is one of a pin and a cavity;
      wherein the plurality of legs are configured to be deployed relative to the upwardly extending post in a deployed state and collapsed relative to the upwardly extending post in a collapsed state;
      wherein, when the plurality of legs are deployed relative to the upwardly extending post in the deployed state, the plurality of legs are spaced radially from a bottom end of the upwardly extending post and ends of the plurality of legs are spaced from the longitudinal post axis; and
      wherein, as the plurality of legs are collapsed relative to the upwardly extending post from the deployed state to the collapsed state, the ends of the plurality of legs move closer to the longitudinal post axis; and
   a saddle configured to support an arm of a user, the saddle comprising:
      a top portion having two spaced ends and defining an upper arm-supporting surface, wherein the upper arm-supporting surface is configured to support the arm of the user;
      an upper support portion having two spaced ends;
      a lower support portion; and a lower area;
wherein the saddle defines an attachment portion at the lower area;
wherein the attachment portion defined by the saddle is the other of the pin and the cavity;
wherein the pin is configured to fit into the cavity to attach the saddle to the upwardly extending post;
wherein the saddle is generally U-shaped along a width of the saddle, thereby defining a low point in a middle section of the upper arm-supporting surface to support an elbow region of the arm of the user with the arm of the user lying across the width of the saddle;
wherein the saddle has a height orthogonal to the width of the saddle;
wherein the saddle has a thickness orthogonal to the width of the saddle and the height of the saddle;
wherein the saddle is wider at the upper support portion than at the lower area;
wherein the saddle is thicker at the upper support portion than at the lower support portion;
wherein the lower support portion is tapered from the upper support portion to the lower area;
wherein each of the two spaced ends of the top portion rolls over a respective one of the two spaced ends of the upper support portion and extends downwardly therefrom; and
wherein the upwardly extending post is adjustable relative to the plurality of legs to allow the saddle to be positioned at an appropriate height such that the arm of the user, when supported by the saddle, is in a horizontal position.

2. The arm support of claim 1, wherein the upper arm-supporting surface of the top portion of the saddle is textured to provide grip of the arm of the user.

3. The arm support of claim 1, wherein the upwardly extending post comprises a plurality of telescopic post sections to allow a height adjustment of the adjustable stand.

4. The arm support of claim 1, wherein the adjustable stand further comprises:
a central knuckle; and
a plurality of pivoting arms;
wherein the plurality of legs are supported from the central knuckle by the plurality of pivoting arms to allow the plurality of legs to be folded from the deployed state to the collapsed state.

5. The arm support of claim 1, wherein the adjustable stand further comprises a plurality of casters coupled to the plurality of legs to allow the arm support to move.

6. The arm support of claim 1, wherein the lower support portion is a support structure tapering evenly to the lower area, and wherein the upper support portion is a support cushion positioned between the top portion and the support structure.

7. The arm support of claim 1, wherein the pin and the cavity are threaded to removably attach the saddle to the upwardly extending post.

8. The arm support of claim 1, wherein the attachment portion defined by the upwardly extending post is the cavity, and wherein the attachment portion defined by the saddle is the pin.

9. The arm support of claim 1, wherein the longitudinal post longitudinal axis is vertical.

10. The arm support of claim 1, wherein the longitudinal post axis is angled from a vertical axis.

11. The arm support of claim 1, wherein the saddle is approximately 4 inches high, 1.5 inches thick, and 7.5 inches wide.

12. An arm support adapted to be used for blood pressure monitoring, the arm support comprising:
an adjustable stand comprising:
a plurality of legs; and
an upwardly extending post that is supported by the plurality of legs and lies along a longitudinal post axis;
wherein the adjustable stand has an adjustable height;
wherein the upwardly extending post defines an attachment portion at a top end of the upwardly extending post;
wherein the attachment portion defined by the upwardly extending post is one of a pin and a cavity;
wherein the upwardly extending post comprises a plurality of telescopic post sections to allow a height adjustment of the adjustable stand;
wherein the plurality of legs are configured to be deployed relative to the upwardly extending post in a deployed state and collapsed relative to the upwardly extending post in a collapsed state;
wherein, when the plurality of legs are deployed relative to the upwardly extending post in the deployed state, the plurality of legs are spaced radially from a bottom end of the upwardly extending post and ends of the plurality of legs are spaced from the longitudinal post axis; and
wherein, as the plurality of legs are collapsed relative to the upwardly extending post from the deployed state to the collapsed state, the ends of the plurality of legs move closer to the longitudinal post axis; and
a saddle configured to support an arm of a user, the saddle comprising:
a top portion having two spaced ends and defining an upper arm-supporting surface, wherein the upper arm-supporting surface is configured to support the arm of the user;
an upper support portion having two spaced ends;
a lower support portion; and
a lower area;
wherein the saddle defines an attachment portion at the lower area;
wherein the attachment portion defined by the saddle is the other of the pin and the cavity;
wherein the pin is configured to fit into the cavity to attach the saddle to the upwardly extending post;
wherein the upper arm-supporting surface is textured to provide grip of the arm of the user;
wherein the saddle is generally U-shaped along a width of the saddle, thereby defining a low point in a middle section of the upper arm-supporting surface to support an elbow region of the arm of the user with the arm of the user lying across the width of the saddle;
wherein the saddle has a height orthogonal to the width of the saddle;
wherein the saddle has a thickness orthogonal to the width of the saddle and the height of the saddle;
wherein the saddle is wider at the upper support portion than at the lower area;
wherein the saddle is thicker at the upper support portion than at the lower support portion;
wherein the lower support portion is tapered from the upper support portion to the lower area;

wherein each of the two spaced ends of the top portion rolls over a respective one of the two spaced ends of the upper support portion and extends downwardly therefrom; and wherein the upwardly extending post is adjustable relative to the plurality of legs to allow the saddle to be positioned at an appropriate height such that the arm of the user, when supported by the saddle, is in a horizontal position.

13. The arm support of claim 12, wherein the adjustable stand further comprises:

a central knuckle; and a plurality of pivoting arms;

wherein the plurality of legs are supported from the central knuckle by the plurality of pivoting arms to allow the plurality of legs to be folded from the deployed state to the collapsed state.

14. The arm support of claim 12, wherein the adjustable stand further comprises a plurality of casters coupled to the plurality of legs to allow the arm support to move.

15. The arm support of claim 12, wherein the lower support portion is a support structure tapering evenly to the lower area, and wherein the upper support portion is a support cushion positioned between the top portion and the support structure.

16. The arm support of claim 12, wherein the pin and the cavity are threaded to removably attach the saddle to the upwardly extending post.

17. The arm support of claim 12, wherein the attachment portion defined by the upwardly extending post is the cavity, and wherein the attachment portion defined by the saddle is the pin.

18. The arm support of claim 12, wherein the longitudinal post axis is vertical.

19. The arm support of claim 12, wherein the longitudinal post axis is angled from a vertical axis.

20. The arm support of claim 12, wherein the saddle is approximately 4 inches high, 1.5 inches thick, and 7.5 inches wide.

* * * * *